United States Patent [19]

Ponsford et al.

[11] 4,245,089

[45] Jan. 13, 1981

[54] NOVEL INTERMEDIATES FOR β-LACTAMS

[75] Inventors: Roger J. Ponsford, Horsham; Robert Southgate, Warnham, Nr. Horsham, both of England

[73] Assignee: Beecham Group Limited, England

[21] Appl. No.: 6,435

[22] Filed: Jan. 25, 1979

[30] Foreign Application Priority Data

Feb. 2, 1978 [GB] United Kingdom ............... 04178/78

[51] Int. Cl.³ ............................................. C07D 265/12
[52] U.S. Cl. .................................. 544/71; 260/239 A; 544/90; 544/162; 544/175; 424/244
[58] Field of Search ..................................... 544/90, 71

[56] References Cited

FOREIGN PATENT DOCUMENTS 4880 of 1977 Denmark ................................... 544/90

*Primary Examiner*—John D. Randolph
*Attorney, Agent, or Firm*—Jacobs & Jacobs

[57] ABSTRACT

Compounds of the formula (III):

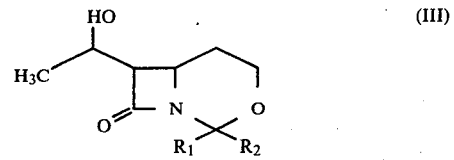

wherein $R_1$ is alkyl of up to 3 carbon atoms and $R_2$ is alkyl of up to 3 carbon atoms optionally joined to $R_1$ so that $R_1$ and $R_2$ and the carbon atom to which they are attached form a spiro-cyclopentyl or spiro-cyclohexyl ring, and wherein the configuration about the β-lactam ring is trans, are useful in the preparation of antibacterial β-lactam compounds.

A process for the preparation of the compounds of the formula (III), is also desired.

7 Claims, No Drawings

NOVEL INTERMEDIATES FOR β-LACTAMS

The present invention relates to chemical intermediates and to a process for their preparation.

Danish Patent Application No. 4880/77 disclosed inter alia that the compounds of the formula (I):

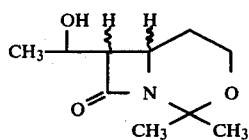

could be converted into the useful antibacterial agents of the formula (II):

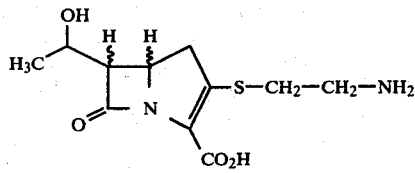

We have now found a class of compounds that may be converted by the process of Danish Patent Application No. 4880/77 to the compounds of the formula (II) having the trans-configuration about the β-lactam rng substantially free of the corresponding cis isomers.

Accordingly the present invention provides the compounds of the formula (III):

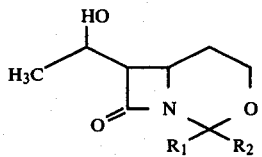

wherein $R_1$ is an alkyl groups of up to 3 carbon atoms and $R_2$ is an alkyl group of up to 3 carbon atoms optionally joined to $R_1$ so that $R_1$ and $R_2$ and the carbon atom to which they are attached form a spiro-cyclopentyl or spirocyclohexyl ring, and wherein the configuration about the β-lactam ring is trans.

Suitably $R_1$ is a methyl group and $R_2$ is a methyl group.

Suitably $R_1$ and $R_2$ together with the carbon atom to which they are attached form a spiro-cyclohexyl ring.

The present invention also provides a process for the preparation of a compound of the formula (III) which comprises the reduction of a corresponding compound of the formula (IV):

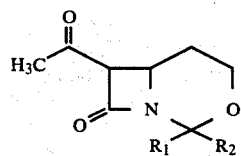

wherein $R_1$, $R_2$ and the configuration about the β-lactam ring are as defined in relation to formula (III).

The compounds of the formula (IV) may be reduced in conventional manner by reaction with a complex hydride. A particularly suitable method of reduction employs sodium borohydride at a slightly depressed temperature, for example at about 0° C., in an alcoholic solvent such as ethanol.

The compounds of the formula (IV) may be prepared by the following reaction scheme:

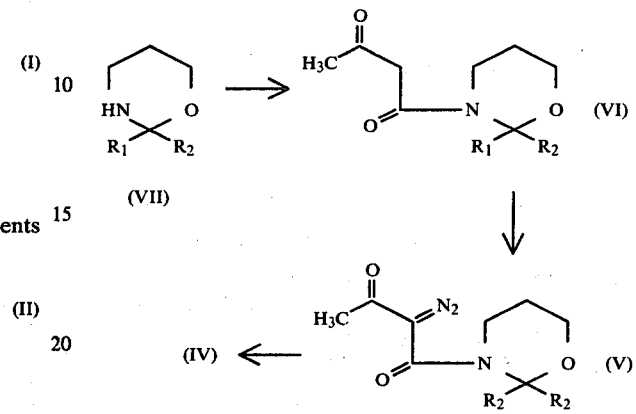

The diazo compounds of the formula (V) may be ring-closed by photolysis, for example by irradiation with a 450 w Hanovia medium pressure mercury lamp with a pyrex reaction vessel. Generally, the photolysis reaction is carried out at a depressed temperature, for example −20° to −80° C., in an inert solvent such as diethyl ether.

While the ring-closing reaction produces the trans configuration about the β-lactam ring, the product of the reaction is a mixture of the two optical isomers. Reduction of this mixture produces a mixture of the isomers of the formulae (IX)–(XII):

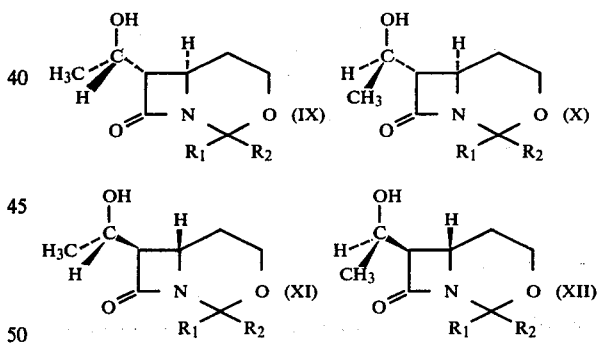

This mixture may be separated, for example, by chromatography on silica gel, into two pairs of enantiomers, i.e. (IX) and (XII), and (X) and (XI).

The diazo compounds of the formula (V) may be prepared by the diazotization of a corresponding compound of the formula (VI) by reaction with a diazotizing agent such as tosyl azide in the presence of a tertiary base such as triethylamine. Generally the reaction is performed in an organic solvent such as acetonitrile at an approximately ambient temperature.

The amides of the formula (VI) may be prepared by the acylation of corresponding compounds of the formula (VII), for example by reaction with diketene in ethanolic solution at a depressed temperature.

The oxazines of the formula (VII) may be prepared by the method of Hancock et al, *J. Amer. Chem. Soc.*, 1944, 66, 1947.

The hydroxyl group of the formula (III) may also be derivatised if desired. For example, the hydroxyl group may be acylated to yield a corresponding compound of the formula (VIII):

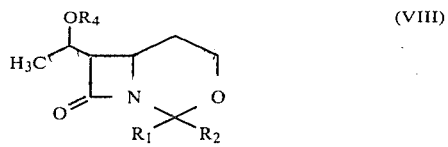

wherein $R_1$, $R_2$ and the configuration about the β-lactam ring are as defined in relation to formula (III) and $R_4$ is an acyl group. Such acylated compounds are also part of this invention as they also may be used in the preparation of antibacterial agents by the method of Danish Application No. 5234/76, which relates to compounds analogous to those of the formula (II), in which the hydroxyl group is replaced by an acyloxy group.

Particularly suitable acyl groups $R_4$ include those of the sub-formula —CO—$R_3$ or —COOR$_3$ is an alkyl group of up to 3 carbon atoms or a phenyl, benzyl, phenoxymethyl or p-nitrobenzyl group.

EXAMPLE 1

Preparation of 3-acetoacetyl-2,2-dimethyltetrahydro-1,3-oxazine and 3-acetoacetyl-2,2-spirocyclohexyltetrahydro-1,3-oxazine.

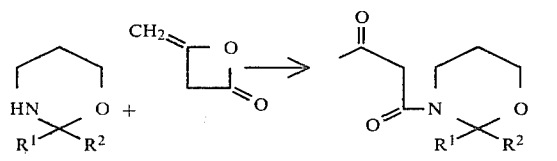

2,2-Dimethyltetrahydro-1,3-oxazine (1; $R^1=R^2=CH_3$) (4.56 g) was dissolved in ethanol (50 ml) and diketene (2) (freshly distilled) (3.36 g) was added at 5° C. The mixture was stirred at room temperature for three hours. Evaporation of the solvent and chromatography yielded the product (3; $R_1=R_2=CH_3$) (4 g; 60%) as an oil; $\nu_{max}$ (CHCl$_3$) 1720, 1640 cm$^{-1}$. δ ppm (CDCl$_3$) 1.64 (6H, s, (C$\underline{H}_3$)$_2$). 1.90 (2H, m, C$\underline{H}_2$), 2.21 (3H, s, COC$\underline{H}_3$), 3.39 (2H, t, J 7 Hz, NC$\underline{H}_2$), 3.47 (2H, s, COC$\underline{H}_2$CO), 3.80 (2H, t, J 7 Hz, OC$\underline{H}_2$).

Similarly, 2,2-spirocyclohexyltetrahydro-1,3-oxazine (1; $R^1R^2$=(CH$_2$)$_5$) gave 2,2-spirocyclohexyltetrahydro-1,3-oxazine (3; $R^1R^2$=(CH$_2$)$_5$) in 73% yield as an oil after chromatography; $\nu_{max}$ (CHCl$_3$) 1720, 1635 cm$^{-1}$. δ ppm (CDCl$_3$) 1.20 to 2.90 (12H, complex pattern, ring C$\underline{H}_2$'s), 2.21 (3H, s, COC$\underline{H}_3$), 3.37 (2H, t, 7 Hz, NC$\underline{H}_2$), 3.44 (2H, s, COC$\underline{H}_2$CO), 3.76 (2H, t, J 7 Hz, OC$\underline{H}_2$) (Found: M 239.1520, C$_{13}$H$_{21}$NO$_3$ requires 239.1521).

EXAMPLE 2

Preparation of 3-acetodiazoacetyl-2,2-dimethyltetrahydro-1,3-oxazine and 3-acetodiazoacetyl-2,2-spirocyclohexyltetrahydro-1,3-oxazine.

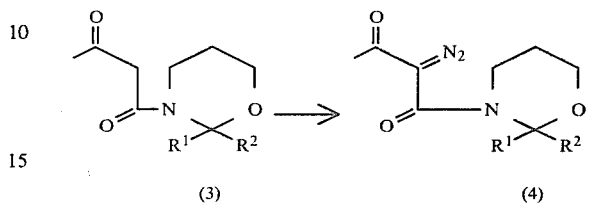

3-Acetoacetyl-2,2-dimethyltetrahydro-1,3-oxazine (3; $R^1=R^2=CH_3$) (3.00 g) was dissolved in acetonitrile (25 ml) and treated with Et$_3$N (1.5 g) and tosyl azide (4.5 g; 1.5 equivs.). The mixture was stirred at room temperature overnight, the solvent evaporated and the residue chromatographed to yield the diazo-compound (4; $R^1=R^2=CH_3$) as an oil (3 g; 89%); $\nu_{max}$ (CHCl$_3$) 2100, 1645, 1615 cm$^-$. δ ppm (CDCl$_3$) 1.66 (6H, s, (C$\underline{H}_3$)$_2$), 1.90 (2H, m, C$\underline{H}_2$), 2.32 (3H, s, COC$\underline{H}_3$), 3.50 (2H, t, J 7 Hz, N—C$\underline{H}_2$), 3.88 (2H, t, J 7 Hz, OC$\underline{H}_2$).

Similarly 3-acetoacetyl-2,2-spirocyclohexyltetrahydro-1,3-oxazine (3; $R^1R^2$=(CH$_2$)$_5$) gave 3-acetodiazoacetyl-2,2-spirocyclohexyltetrahydro-1,3-oxazine in 72% yield as an oil after chromatography, which solidified on standing mp 31° C; $\nu_{max}$ (CHCl$_3$) 2100, 1645, 1615 cm$^{-1}$. δ ppm (CDCl$_3$) 1.20 to 2.90 (12H, complex pattern, ring C$\underline{H}_2$'s), 2.36 (3H, s, COC$\underline{H}_3$), 3.53 (2H, t, J 7 Hz, N—C$\underline{H}_2$), 3.92 (2H, t, J 7 Hz,OC$\underline{H}_2$).

EXAMPLE 3

Preparation of 7-acetyl-2,2-dimethyl-8-oxo-3-oxa-1-azabicyclo[4.2.0]octane and 7-acetyl-2,2-spirocyclohexyl-8-oxo-3-oxa-1-azabicyclo[4.2.0]octane.

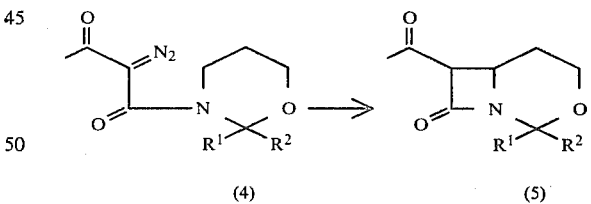

The diazo-compound (4; $R^1=R^2=CH_3$) (2 g) was dissolved in freshly-distilled ether (700 ml) and degassed at −60° C. for ten minutes. Photolysis of the solution at −60° C. using a Hanovia 450 w medium pressure mercury lamp and pyrex reaction vessel over 8 h while the solution gradually warmed to −20° C. gave the product (5; $R^1=R^2=CH_3$) as an oil after chromatography (1.2 g; 55%); $\nu_{max}$ (CHCl$_3$) 1750, 1715 cm$^{-1}$. δ ppm (CDCl$_3$) 1.43 and 1.70 (6H, two singlets, (C$\underline{H}_3$)$_2$), 1.80–2.20 (2H, m, C5-CH$_2$), 2.34 (3H, s, COC$\underline{H}_3$), 3.70 to 4.20 (4H, complex pattern, C6-H, C7-H and C4-CH$_2$).

Similarly the diazo-compound (4; $R^1R^2$=(CH$_2$)$_5$) gave 7-acetyl-2,2-spirocyclohexyl-8-oxo-3-oxa-1-azabicyclo-[4,2,0]octane (5; $R^1R^2$=(CH$_2$)$_5$) in 73% yield after chromatography; $\nu_{max}$ (CHCl$_3$) 1750, 1710 cm$^{-1}$. δ ppm (CDCl$_3$) 1.20 to 2.50 (12H, complex pattern, ring CH$_2$'s), 2.35 (3H, s, COCH$_3$), 3.70 to 4.30 (4H, complex pattern C6-H, C7-H and C4-CH$_2$) (Found: M 237.1373. C$_{13}$H$_{19}$NO$_3$ requires M 237.1372).

EXAMPLE 4

Preparation of 7-(1'-hydroxyethyl)-2,2-dimethyl-8-oxo-3-oxa-1-azabicyclo[4.2.0]octane and 7-(1'-hydroxyethyl)-2,2-spirocyclohexyl-8-oxo-3-oxa-1-azabicyclo[4.2.0]octane.

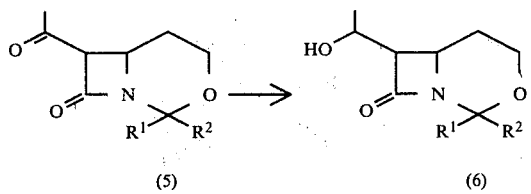

(5) (6)

The acetyl derivative (5; R$^1$=R$^2$=CH$_3$) (0.99 g) was dissolved in ethanol (10 ml) and NaBH$_4$ (0.1 g) in ethanol (5 ml) was added at 0°. The reaction was stirred at 0° for 30 min, the solvent evaporated and the residue chromatographed to yield the product (6; R$^1$=R$^2$=CH$_3$) (0.75 g; 75%); $\nu_{max}$ (CHCl$_3$) 3450, 1740 cm$^{-1}$. δ ppm (CDCl$_3$) 1.32 (3H, d, J 6.5 Hz, CH$_3$CH), 1.43 (3H, s, CH$_3$), 1.60–2.00 (2H, m, C5-CH$_2$), 1.75 (3H, s, CH$_3$), 2.89 (1H, m, C7-H), 3.56 (1H, m, C6-H), 3.90 (2H, m, OCH$_2$), 4.17 (2H, br. m. CH$_3$CHOH and OH [exchangeable]. M$^+$ at m/e 199.

The acetyl derivative (5; R$^1$, R$^2$=(CH$_2$)$_5$) similarly gave the product (6; R$^1$, R$^2$=(CH$_2$)$_5$ in 69% yield at an oil after chromatography; $\nu_{max}$ (CHCl$_3$), 3450, 1740 cm$^{-1}$. δ ppm (CDCl$_3$) 1.26 (3H, d, J 6.5 Hz, CH$_3$CH), 1.20 to 2.40 (12H, complex pattern ring CH$_2$'s) 2.73 (1H, dd, J 2 Hz, J$^1$ 6.5 Hz, C7-H), 2.62 (1H, br.s, OH [exchangeable]), 3.52 (1H, ddd, J 2 Hz, J' 6.5 Hz, J'' 10 Hz, C6-H), 3.81 (2H, m, OCH$_2$), 4.04 (1H, m, CH$_3$CHOH). M$^+$ at m/e 239.

EXAMPLE 5

Preparation of 7-(1'-phenoxyacetoxyethyl)-2,2-dimethyl-8-oxo-3-oxa-1-azabcicylo[4.2.0]octane.

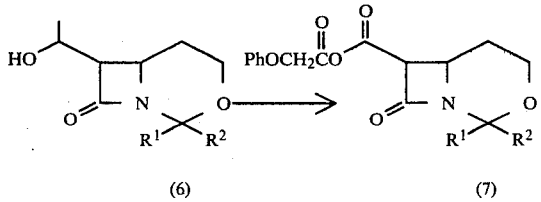

(6) (7)

The carbinol (6; R$^1$=R$^2$=CH$_3$) (500 mg) was dissolved in methylene chloride (10 ml) and cooled to −5° C. Pyridine (230 mg) was added, followed by phenoxyacetyl chloride (430 mg). The mixture was stirred at 0° C. for two hours, and the solution was then washed with 20% citric acid (3×10 ml) and 3% NaHCO$_3$ (3×10 ml) and dried over MgSO$_4$. Evaporation of the solvent and chromatography gave the product (7; R$^1$=R$^2$=CH$_3$) as an oil (420 mg; 50%); $\nu_{max}$ (CHCl$_3$) 1750, 1600 cm$^{-1}$. δ ppm (CDCl$_3$) 1.32 (3H, s, CH$_3$), 1.36 (3H, d, J 7 Hz, CHCH$_3$), 1.65 and 1.68 (3H, two singlets, CH$_3$ for two isomers), 1.50–1.82 (2H, m, C5-CH$_2$), 2.86 and 2.98 (1H, two double doublets J 8.5 Hz, J$^1$ 2 Hz and J 5 Hz, J$^1$ 2 Hz respectively, C7-H), 3.30 (1H, m, C6-H), 3.74 (2H, br. m., OCH$_2$), 4.57 (2H, s, PhOCH$_2$), 5.21 and 5.31 (1H, two multiplets, CH$_3$CH for two isomers), 7.05 (5H, m, PhOCH$_2$(Found: M 333.1591. C$_{18}$H$_{23}$NO$_5$ requires 333.1576.

EXAMPLE 6

7-(1'-Phenoxyacetoxyethyl)-2,2-spirocyclohexyl-8-oxo-3-oxa-1-azabicyclo[4.2.0]octane

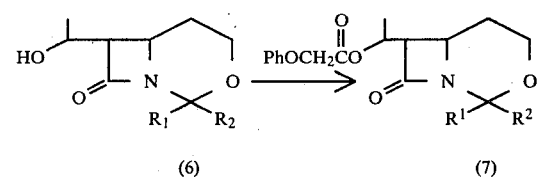

(6) (7)

The carbinol (6; R$_1$R$_2$=(CH$_2$)$_5$) (239 mg) was dissolved in ethyl acetate (20 ml) and cooled to 0°. Phenoxyacetic acid (170 mg) was added followed by D.C.C.I. (275 mg). The mixture was stirred at RT for one hour, pyridine (200 mg) was added. The reaction was left stirring overnight and filtered. The solution was washed with 20% citric acid (5 ml) and 3% NaHCO$_3$ solution (3×10 ml) and dried over MgSO$_4$. The solvent was evaporated and the residue chromatographed (Kieselgel 60, <230 mesh) to yield the product (7; R$_1$R$_2$=(CH$_2$)$_5$) as a mixture of isomers (0.25 g) which were separable by chromatography on kieselgel 60 (<230 mesh):

Isomer I $\nu_{max}$ (CHCl$_3$) 1750, 1600 cm$^{-1}$. δ ppm (CDCl$_3$) 1.41 (3H, d, J 7 Hz, CHCH$_3$) 1.0 to 2.70 (12H, complex pattern, ring CH$_2$'s), 2.88 (1H, dd, J 2 Hz, J$^1$ 8.5 Hz, C7-H), 3.34 (1H, br.t., J 7 Hz, C6-H), 3.82 (2H, br.m., OCH$_2$), 4.67 (2H, s, PhOCH$_2$), 5.30 (1H, br. m, CH$_3$CH), 7.20 (5H, m, PhO) M$^+$ at m/e 373.

Isomer II $\nu_{max}$ (CHCl$_3$) 1750, 1600 cm$^{-1}$, δ ppm (CHCl$_3$) 1.42 (3H, d, J 7 Hz, CHCH$_3$), 1.10 to 2.50 (12H, complex pattern, ring CH$_2$'s), 2.98 (1H, dd, J 2 Hz, J$^1$ 5 Hz, C7-H), 3.33 (1H, m, C6-H), 3.82 (2H, br.m., OCH$_2$), 4.66 (2H, s, PhOCH$_2$), 5.35 (1H, br.m, CH$_3$CH), 7.15 (5H, m, PhO), M$^{30}$ at m/e 373.

What we claim is:
1. Process for the preparation of 7-(1-hydroxyethyl)-8-oxo-3-oxa-1-azabicyclo[4.2.0]octane of the formula:

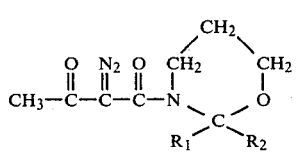

wherein each of R$_1$ and R$_2$ is alkyl of 1 to 3 carbon atoms or together tetramethylene or pentamethylene and the configuration about the β-lactam ring is trans which comprises, effecting cyclization of an oxazine of the formula:

photolytically to yield a 7-acetyl-8-oxo-3-oxa-1-azabicyclo [4.2.0]octane of the formula:

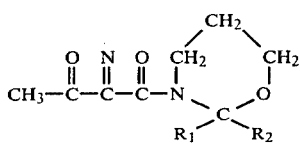

and the reduction of said 7-acetyl compound.

2. The process according to claim 1 wherein said reduction is effected with sodium borohydride.

3. The process according to claim 2 which includes the step of separating two pairs of enantiomorphs generated upon said reduction.

4. A compound of the formula:

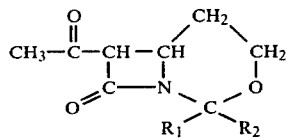

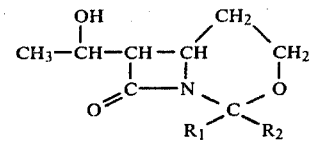

wherein $R_1$ and $R_2$ together are tetramethylene or pentamethylene and the configuration about the $\beta$-lactam ring is trans.

5. The compound according to claim 4 wherein $R_1$ and $R_2$ are pentamethylene.

6. A compound of the formula:

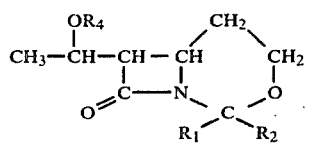

wherein
$R_4$ is acyl, and
$R_1$ and $R_2$ together are tetramethylene or pentamethylene and the configuration about the $\beta$-lactam ring is trans.

7. The compound according to claim 6 wherein $R_4$ is

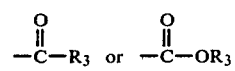

in which $R_3$ is alkyl of 1 to 3 carbon atoms, phenyl, benzyl, phenoxymethyl or p-nitrobenzyl.

* * * * *